United States Patent [19]

Osterried et al.

[11] Patent Number: 5,690,857

[45] Date of Patent: Nov. 25, 1997

[54] THERMOCHROMIC EFFECT PIGMENT AND PROCESS FOR PRODUCING THE SAME

[75] Inventors: Karl Osterried, Dieburg; Magarete Herbski, Ober-Ramstadt, both of Germany; Ian Charles Sage, Dorset, Great Britain

[73] Assignee: Merck Patent Gesellschaft Mit Beschrankter Haftung, Darmstadt, Germany

[21] Appl. No.: 244,617

[22] PCT Filed: Dec. 3, 1992

[86] PCT No.: PCT/EP92/02799

§ 371 Date: Jun. 7, 1994

§ 102(e) Date: Jun. 7, 1994

[87] PCT Pub. No.: WO93/12195

PCT Pub. Date: Jun. 24, 1993

[30] Foreign Application Priority Data

Dec. 9, 1991 [EP] European Pat. Off. ............ 911211007

[51] Int. Cl.⁶ ............................ C09K 19/00; C08K 5/00; A61K 7/021; C09D 11/00
[52] U.S. Cl. ............................ 252/299.1; 252/299.01; 106/493; 106/498; 106/22 C; 106/172.1; 424/401; 424/63; 424/70.6; 501/17; 349/90; 349/106
[58] Field of Search ...................... 252/299.1, 299.01, 252/586; 345/106; 349/90, 106; 359/288; 428/933; 430/964; 106/493, 498, 22 C, 172.1; 424/401, 63, 70.6; 501/17

[56] References Cited

U.S. PATENT DOCUMENTS

| 2,800,457 | 7/1957 | Green et al. | 428/402.2 |
| 5,026,429 | 6/1991 | Mronga et al. | 106/493 |
| 5,188,815 | 2/1993 | Coates et al. | 424/7.1 |
| 5,194,183 | 3/1993 | Munch et al. | 252/586 |
| 5,338,566 | 8/1994 | Gregory et al. | 427/8 |
| 5,376,699 | 12/1994 | Sage et al. | 523/206 |
| 5,562,763 | 10/1996 | Brucker et al. | 106/493 |

FOREIGN PATENT DOCUMENTS

| 0 357 844 | 3/1990 | European Pat. Off. |
| 27 46 228 | 4/1979 | Germany |
| WO91/13125 | 9/1991 | WIPO |

*Primary Examiner*—Richard D. Lovering
*Assistant Examiner*—Daniel S. Metzmaier
*Attorney, Agent, or Firm*—Millen, White, Zelano & Branigan, P.C.

[57] ABSTRACT

A thermochromic effect pigment comprising a thermochromic liquid crystal material encapsulated with a polymer and coated with one or more inorganic metal oxides or nearly insoluble metal salts selected from $Al_2O_3$, $SnO_2$, $ZrO_2$, $TiO_2$, $CaO$, $SiO_2$, $ZnO$, $MgO$ or $BaSO_4$. The pigment is stable in solvent-based formulations and can be used as a colorant in the form of an aqueous suspension or as a powder in lacquer compositions, plastic compositions, dyed filter compositions, dyed glass compositions, dyed cosmetic compositions, printing ink compositions, and in hair coloring agents.

21 Claims, No Drawings

THERMOCHROMIC EFFECT PIGMENT AND PROCESS FOR PRODUCING THE SAME

This application is filed under 35 U.S.C. 371 and based on PCT/EP92/02799, filed Dec. 3, 1992.

The invention relates to a thermochromic effect pigment comprising a thermochromic liquid crystal material encapsulated with a polymer and coated with one or more inorganic metal oxides or nearly insoluble metal salts.

BACKGROUND OF THE INVENTION

There is a continuously increasing demand for liquid crystal pigment as a coating layer onto a substrate or for use in printing, in lacquer formulations, in plastics and cosmetics. At present, for make-up cosmetics, such as foundations, eye shadows, cheek rouges and other cosmetics thermochromic effect pigments are desired because of their color play.

EP-A-0 383 376 discloses a liquid crystal pigment consisting of a lamellar particle which is coated with a liquid crystalline material. The pigment is manufactured by dissolving a liquid crystalline material in a suitable solvent, dispersing a lamellar particle in the solvent and coating the lamellar particle by precipitating a portion of the liquid crystalline material from the solution onto the lamellar particle. This pigment has the disadvantage that it is not resistant against solvents, has low mechanical stability and poor flowability.

SUMMARY OF THE INVENTION

Accordingly, it is an object of the present invention to provide thermochromic effect pigments with improved resistance against solvents and good mechanical stability and flowability so that they can be used like a common pigment. Furthermore, it is an object of the present invention to modify color play and color change in a definite way.

This object is accomplished according to the present invention by a thermochromic effect pigment comprising an encapsulated thermochromic liquid crystal which is coated with one or more inorganic metal oxides, mixtures of inorganic metal oxides, or nearly insoluble metal salts.

Furthermore, this object is accomplished according to the present invention by a process for preparing thermochromic effect pigments by precipitating a metal oxide or metal salt in an aqueous suspension onto the encapsulated liquid crystal in a well-known manner.

The inorganic metal oxides or metal salts can be selected for example from $Al_2O_3$, $SnO_2$, CaO, $SiO_2$, $ZrO_2$, $TiO_2$, ZnO, MgO or $BaSO_4$ and can be precipitated on to the encapsulated liquid crystal as a single oxide or as a mixed oxide thereof. The mixed oxide preferably contains silicon dioxide. The amount of metal oxides or salts in the thermochromic effect pigment as a rule is from 2 to 50%, preferably from 5 to 15% by weight, relative to total pigment weight.

The encapsulated thermochromic liquid crystal material is a commercially available material. The liquid crystals are encapsulated by complex coacervation in gelatin and gum arabic (U.S. Pat. No. 2,800,457), coacervation in gelatin (U.S. Pat. reissue 24,899), by interfacial polymerization in polyester (U.S. Pat. No. 3,429,827), by interfacial polymerisation in polyamide (U.S. Pat. No. 3,208,951) or other processes well known in the art.

The amount of polymer in the encapsulated thermochromic liquid crystal material is from 0.1 to 25%, preferably 2 to 10% by weight, relative to total weight of the encapsulated liquid crystal material.

A suitable thermochromic liquid crystal material is Licritherm® TCC-1001 consisting of a thermochromic liquid crystal encapsulated with gelatin manufactured by Merck Ltd.

The liquid crystal is an admixture of at least three chiral components and optionally at least one non-chiral component. At least one chiral component is a compound of the formulae I or II

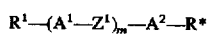

$$R^1—(A^1—Z^1)_m—A^2—R*$$  I wherein $R^1$ is $R^*$ or an alkyl radical or an alkenyl radical with up to 18 C atoms optionally substituted by CN or at least one halogen atom, wherein one or two non-adjacent $CH_2$ groups of this radicals can also be replaced by —O—, —CO—, —O—CO— and/or —CO—O—, $A^1$ and $A^2$ are in each case independently of one another a) a 1,4-cyclohexylene group, wherein one or two non-adjacent $CH_2$ groups can also be replaced by —O— and/or —S— and/or which can be substituted in the 1-position by a CN— or $CH_3$-group, b) a 1,4-cyclohexenylene, a piperidine-1,4-diyl or 1,4-bicyclo[2.2.2]octylene group, or c) a 1,4-phenylene group optionally substituted by one or two F-atoms or one or two CN— or one or two $CH_3$-groups, wherein at least one CH group can also be replaced by N, $Z^1$ is —CO—O—, —O—CO—, —$CH_2CH_2$—, —CHCN—$CH_2$—, —$CH_2$—CHCN—, CH≡CH, —$OCH_2$—, —$CH_2O$—, —CH=N—, —N=CH—, —NO=N, —N=NO— or a single bond, m is 0, 1, 2 or 3, and $R^*$ is a chiral radical imparting optical activity to the compound of the formula I;

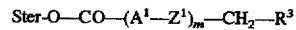

$$Ster—O—CO—(A^1—Z^1)_m—CH_2—R^3$$  II wherein $A^1$, $Z^1$ and m have the meaning giving for formula I, and $R^3$ is a normal or branched alkyl or alkenyl radical with up to 16 C atoms wherein one $CH_2$ group may be replaced by —O—, —O—CO— or —CO—O—, and Ster denotes a saturated or unsaturated gonan-3-yl group being optionally substituted by up to 6 normal or branched alkyl radicals with 1 to 10 C atoms.

$R^*$ can also be a chiral radical of the formula III

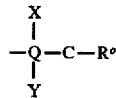

$$\begin{array}{c} X \\ | \\ —Q—C—R^o \\ | \\ Y \end{array}$$  III wherein

Q is a single bond or an alkylene group with 1–8 C atoms, wherein one or two non-adjacent $CH_2$ groups can be replaced by —CH(CN)—, —CH(F)—, —CH(Cl)—, —O—, —S—, —CO—O— or O—CO X is H or $CH_3$ Y is F, Cl, Br, CN or $CH_3$ $R^o$ is an alkyl residue being different from X with up to 14 C atoms, wherein one or two non-adjacent $CH_2$ groups may be replaced by —O—, —CO—O— or —O—CO—.

Furthermore at least one non-chiral compound is a compound of the formula IV $$R^2-(A^3-Z^2)_p-A^4-Z^3-A^5-R^4 \quad\quad \text{IV}$$

$R^2$ and
$R^4$ in each case independently of one another are an alkyl radical or an alkenyl radical each with up to 18 C atoms optionally substituted by CN or at least one halogen atom, wherein one or two non-adjacent $CH_2$ groups of these radicals can also be replaced by —O—, —CO—, —O—CO— and/or —CO—O—, one of $R^2$ and $R^4$ may also be CN or halogen, $A^3$, $A^4$ and
$A^5$ are in each case independently of one another a) a 1,4-cyclohexylene group, wherein one or two non-adjacent $CH_2$ groups can also be replaced by —O— and/or —S— and/or which can be substituted in the 1-position by a $CH_3$— or CN-group, b) a 1,4-cyclohexenylene, a piperidine-1,4-diyl or 1,4-bicyclo[2,2,2]octylene group, or c) a 1,4-phenylene group optionally substituted by one or two F atoms or one or two $CH_3$— or one or two CN groups $Z^2$ and
$Z^3$ are each —CO—O—, —O—CO—, —CH$_2$CH$_2$—, —CHCN—CH$_2$—, —CH$_2$—CHCN—, —CH=CH—, —OCH$_2$—, —CH$_2$O—, —CH=N—, —N=CH—, —NO=N, —N=NO— or a single bond, and p is 0, 1 or 2.

As thermochromic liquid crystal can also be used Licitherm® TCC-216, a mixture of thermochromic liquid crystal compounds with the following composition (manufactured by Merck Ltd.):

| | |
|---|---|
| CE4 | 23.06% |
| CE4R | 7.72% |
| CE5 | 11.68% |
| CE6 | 18.06% |
| CE7 | 15.03% |
| ME805 | 14.88% |
| CE10MBR | 9.58% |

The designation TCC means that the mixture has been microencapsulated according to the process of U.S. Pat. No. 2,800,457, example 2.

In the above formulation, the compounds listed are as below:

| | |
|---|---|
| CE4 | S-(+)-4-(2-methylbutyl)phenyl 4-n-hexyloxybenzoate |
| CE4R | Racemic 4-(2-methylbutyl)phenyl 4-n-hexyloxybenzoate |
| CE5 | S-(+)-4-(2-methylbutyl)phenyl 4-n-octyloxybenzoate |
| CE6 | S-(+)-4-(2-methylbutyl)phenyl 4-n-decyloxybenzoate |
| CE7 | S-(+)-4-(2-methylbutyl)phenyl 4-n-dodecyloxybenzoate |
| ME805 | 4-n-pentylphenyl 4-n-octyloxy-benzoate |
| CE10MBR | Racemic 4-(2-methylbutyl)phenyl 4-methoxybenzoate |

The encapsulated liquid crystal material is suspended in deionized water in a concentration from 3 to 10% by weight and heated to within the range from room temperature to 100° C., preferably 70° to 80° C. while stirring. The pH value is adjusted to within the range of the corresponding precipitation pH value of the metal hydroxide or metal oxide hydrate or the nearly insoluble metal salt according to known methods for the coating of platelet-like substrates.

The coating with $Al_2O_3$ is described in DE-B-24 29 762 and the coating with $SiO_2$ in DE-B-21 06 613. DE-B-2 522 573 and EP-B-0 220 509 disclose the coating with $SnO_2$. Finally EP-B-00 82 986 describes the coating with MgO, DE-B-2 009 566 the coating with $TiO_2$, EP-A-0 256 417 the coating with ZnO and EP-A-0 268 918 the coating with ZrO. The precipitation of barium sulfate onto flaky pigments is described in EP-A-142 695.

After adjustment of the pH value an aqueous solution of a metal salt is added. The solution pH is maintained substantially constant by means of a dilute base. Subsequently, the suspension is cooled, sucked off and washed with deionized water and then the coated liquid crystal material is dried for 3 to 10 minutes, preferably 4 to 6 minutes at 90° to 130° C., preferably 95° to 110° C. It is also possible to dry the product for a longer period of time (e.g. overnight) at lower temperatures, e.g. 50° to 70° C.

However, it is not necessary to dry the pigment; it may be used in the form of the aqueous final suspension as described above.

The product can also be freeze-dried or spray-dried to a powder.

The thermochromic effect pigment can be used as colorant in lacquer compositions, plastic compositions, dyed filter compositions, dyed glass compositions, dyed cosmetic compositions, printing ink compositions, and in hair coloring agents.

However, the use of the pigment is not limited to these applications.

The pigment according to the present invention has the advantage that it can be used as powder for the above-mentioned applications.

The pigments are stable in solvent-based formulations, as well as in water-born systems.

The invention will now be described more specifically with reference to examples thereof which are not intended to limit the scope of the invention.

EXAMPLE 1

25 g encapsulated liquid crystal material (Licritherm® TCC 216), a 33% aqueous suspension with a dry matter of 8.25 g, is suspended in 750 ml deionized water and heated to 75° C. while stirring.

The pH value is adjusted to 7.0 with 5% NaOH solution. 11.84 g $AlCl_3 \cdot 6H_2O$ in 200 ml water is added to the suspension with a rate of 1.5 ml/min. During the addition of the $AlCl_3$ solution the pH is maintained at 7.0 by the simultaneous addition of 5% NaOH solution. Subsequently, the suspension is cooled, sucked off and washed with 15 l deionized water chloride free and dried for 5 min at 100° C.

EXAMPLE 2

25 g encapsulated liquid crystal material (Licritherm® TCC-1001) with a solid content of 8.25 g is suspended in 750 ml water.

The suspension is heated to 60° C. while stirring and the pH value is adjusted to 9.0 with 5% NaOH solution. Then 1.67 ml sodium water glass solution (dilution 1:1 with water) in 50 ml water are added. During the addition the pH value is maintained at 9.0 by the simultaneous addition of 10% hydrochloric acid. Upon completion the suspension is stirred for 15 minutes. The pH is then lowered to 6.5 and the suspension is stirred for further 15 minutes.

0.49 g $AlCl_3 \cdot 6H_2O$ and 0.29 g $Na_2SO_4$ (anhydrous) are added and the suspension heated to 95° C. for 30 minutes. Subsequently, the suspension is cooled, sucked off, washed and dried over night at 50° C.

EXAMPLE 3

25 g encapsulated liquid crystal material (Licritherm® TCC-1001) with a solid content of 8.25 g is suspended in 750 ml water.

The suspension is heated to 60° C. while stirring and the pH value is adjusted to 9.0 with 5% NaOH solution. Then 2.24 ml sodium water glass solution (dilution 1:1 with water) in 100 ml water are added. During the addition the pH value is maintained at 9.0 by the simultaneous addition of 10% hydrochloric acid. Upon completion the suspension is stirred for 15 minutes. Then the suspension is cooled, sucked off, washed and dried over night at 50° C.

EXAMPLE 4

25 g encapsulated liquid crystal material (Licritherm® TCC-1001) with a solid content of 8.25 g is suspended in 750 ml water.

The suspension is heated to 75° C. while stirring and the pH value is adjusted to 11 with 5% NaOH solution. Then 2.07 g $MgCl_2 \cdot 6H_2O$ in 100 ml water are added. During the addition the pH value is maintained at 11 by the simultaneous addition of 10% NaOH solution. Upon completion the suspension is stirred for 15 minutes. Then the suspension is cooled, sucked off, washed and dried over night at 50° C.

EXAMPLE 5

25 g encapsulated liquid crystal material (Licritherm® TCC-1001) with a solid content of 8.25 g is suspended in 750 ml water.

The suspension is heated to 75° C. while stirring and the pH value is adjusted to 2.0 with 10% hydrochloric acid. Then 2.67 ml $TiCl_4$ solution (366 g/l) in 25 ml water are added. During the addition the pH value is maintained at 2.0 by the simultaneous addition of 10% NaOH solution. Upon completion the suspension is stirred for 15 minutes. Then the suspension is cooled, sucked off, washed and dried over night at 50° C.

EXAMPLE 6

25 g encapsulated liquid crystal material (Licritherm® TCC-1001) with a solid content of 8.25 g is suspended in 750 ml water.

The suspension is heated to 75° C. while stirring and the pH value is adjusted to 1.8 with 5% NaOH solution. Then 0.96 g $SnCl_4 \cdot 5H_2O$ in 100 ml water are added. During the addition the pH value is maintained at 1.8 by the simultaneous addition of 10% NaOH solution. Upon completion the suspension is stirred for 15 minutes. Then the suspension is cooled, sucked off, washed and dried over night at 50° C.

EXAMPLE 7

25 g encapsulated liquid crystal material (Licritherm® TCC-1001) with a solid content of 8.25 g is suspended in 750 ml water.

The suspension is heated to 75° C. while stirring and the pH value is adjusted to 7.0. Then 0.69 g $ZnCl_2$ in 100 ml water are added. During the addition the pH value is maintained at 7.0 by the simultaneous addition of 10% NaOH solution. Upon completion the suspension is stirred for 15 minutes. Then the suspension is cooled, sucked off, washed and dried over night at 50° C.

EXAMPLE 8

25 g encapsulated liquid crystal material (Licritherm® TCC-1001) with a solid content of 8.25 g is suspended in 750 ml water.

The suspension is heated to 75° C. while stirring and the pH value is adjusted to 2.0 with 5% NaOH solution. Then 1.08 g $ZrOCl_2 \cdot 8H_2O$ in 100 ml water are added. During the addition the pH value is maintained at 2.0 by the simultaneous addition of 10% NaOH solution. Upon completion the suspension is stirred for 15 minutes. Then the suspension is cooled, sucked off, washed and dried over night at 50° C.

We claim:

1. A thermochromic effect particulate pigment, comprising a thermochromic liquid crystal material encapsulated within a polymeric encapsulating material and on the outer surface of the encapsulating material a coating comprising one or more inorganic metal oxides or metal oxide hydrates, mixtures of inorganic metal oxides or metal oxide hydrates or $BaSO_4$.

2. A pigment according to claim 1, wherein the coating comprises an inorganic metal oxide selected from the group consisting of $Al_2O_3$, $SnO_2$, CaO, $SiO_2$, $ZrO_2$, $TiO_2$, ZnO or MgO; or $BaSO_4$.

3. A pigment according to claim 1, wherein the coating comprises a mixture of inorganic metal oxides or a mixture of inorganic metal oxide hydrates.

4. A pigment according to claim 3, wherein the mixture of inorganic metal oxides or mixture of inorganic metal oxide hydrates contains silicon dioxide.

5. A pigment according to claim 1, wherein the liquid crystal material is an admixture of at least one chiral component and at least one non-chiral component.

6. A pigment according to claim 5, wherein at least one chiral component is a compound of the formula I $$R^2-(A^1-Z^1)_m-A^2-R^* \qquad I$$

wherein $R^1$ is $R^*$ or an alkyl radical or an alkenyl radical with up to 18 C atoms optionally substituted by CN or at least one halogen atom, wherein one or two non-adjacent $CH_2$ groups of these radicals are optionally replaced by —O—, —CO—, —O—CO— or —CO—O—, $A^1$ and $A^2$ are in each case independently of one another
 a) a 1,4-cyclohexylene group, wherein one or two non-adjacent $CH_2$ groups are optionally replaced by -O— or —S— and which further can be optionally substituted in the 1-position by a CN— or $CH_3$— group,
 b) a 1,4-cyclohexenylene, a piperidine-1,4-diyl or 1,4-bicyclo[2.2.2]octylene group, or
 c) a 1,4-phenylene group optionally substituted by one or two F-atoms or one or two CN— or one or two $CH_3$— groups, wherein at least one CH group is optionally replaced by N, $Z^1$ is —CO—O—, —O—CO—, —$CH_2CH_2$—, —CHCN—$CH_2$—, —$CH_2$—CHCN—, —CH≡CH—, —$OCH_2$—, —$CH_2$—O—, —CH=N—, —N=CH—, —NO=N, —N=NO— or a single bond, m is 0, 1, 2 or 3, and $R^*$ is a chiral radical of the formula III $$-Q-\underset{Y}{\overset{X}{\underset{|}{\overset{|}{C}}}}-R° \qquad III$$

wherein

Z is a single bond or an alkylene group with 1–8 C atoms, wherein one or two non-adjacent $CH_2$ groups can be replaced by —CH(CN)—, —CH(F)—, —CH(Cl)—, —O—, —S—, —CO—O— or —O—CO—, X is H or $CH_3$, Y is F, Cl, Br, CN or $CH_3$, and $R^0$ is an alkyl residue being different from X with up to 14 C atoms, wherein one or two non-adjacent $CH_2$ groups may be replaced by —O—, —CO—O— or —O—CO—.

7. A pigment according to claim 5, wherein at least one chiral component is a steroid ester of the formula II

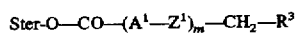

wherein $A^1$ is a) a 1,4-cyclohexylene group, wherein one or two non-adjacent $CH_2$ groups are, optionally, replaced by —O— or —S— and which further can be optionally substituted in the 1-position by a CN— or $CH_3$-group, b) a 1,4-cyclohexenylene, a piperidine-1,4-diyl or 1,4-bicyclo[2,2,2]octylene group, or c) a 1,4-phenylene group optionally substituted by one or two F-atoms or one or two CN— or one or two $CH_3$-groups, wherein at least one CH group is, optionally, replaced by N, $Z^1$ is —CO—O—, —O—CO—, —$CH_2CH_2$—, —CHCN—$CH_2$—, —$CH_2$—CHCN—, —CH=CH—, —$OCH_2$—, —$CH_2$—O, —CH=N—, —N=CH—, —NO=N, —N=NO— or a single bond, m is 0, 1, 2 or 3, and $R^3$ is an alkyl or alkenyl radical with up to 16 C atoms wherein one $CH_2$ group may be replaced by —O—, —O—CO— or —CO—O—, and Ster denotes a saturated or unsaturated gonan-3-yl group being optionally substituted by up to 6 straight chain or branched alkyl radicals with 1 to 10 C atoms.

8. The pigment of claim 1, wherein the amount of the coating is from 2 to 50% by weight relative to the total weight of the pigment.

9. A composition of a pigment according to claim 1 and a solvent.

10. The composition of claim 9, wherein the solvent is a nonaqueous solvent.

11. A pigment according to claim 5 wherein at least one non-chiral compound is a compound of the formula IV

$R^2$ and $R^4$ in each case independently of one another are an alkyl radical or an alkenyl radical each with up to 18 C atoms optionally substituted by CN or at least one halogen atom, wherein one or two non-adjacent $CH_2$ groups of these radicals can also be replaced by —O—, —CO—, —O—CO— or —CO—O—, one of $R^2$ and $R^4$ may also be CN or halogen, $A^3$, $A^4$ and $A^5$ are in each case independently of one another a) a 1,4-cyclohexylene group, wherein one or two non-adjacent $CH_2$ groups can also be replaced by —O— or —S— and which can be substituted in the 1-position by a $CH_3$— or CN-group, b) a 1,4-cyclohexenylene, a piperidine-1,4-diyl or 1,4-bicyclo[2,2,2]octylene group, or c) a 1,4-phenylene group optionally substituted by one or two F atoms or one or two $CH_3$— or one or two CN groups $Z^2$ and $Z^3$ are each —CO—O—, —O—CO—, —$CH_2CH_2$—, —CHCN—$CH_2$—, —$CH_2$—CHCN—, —CH=CH—, —$OCH_2$—, —$CH_2O$—, —CH=N—, —N=CH—, —N=NO—, —NO=N or a single bond, and p is 0, 1 or 2.

12. A colored lacquer composition comprising a pigment of claim 1 as a colorant.

13. A colored paint composition comprising a pigment of claim 1 as a colorant.

14. A colored plastic composition comprising a pigment of claim 1 as a colorant.

15. A dyed filter composition, comprising a pigment of claim 1 as a colorant.

16. A dyed glass composition, comprising a pigment of claim 1 as a colorant.

17. A dyed cosmetic composition, comprising a pigment of claim 1 as a colorant.

18. A printing ink composition, comprising a pigment of claim 1 as a colorant.

19. A hair coloring agent comprising a pigment of claim 1 as a colorant.

20. A process for the production of a thermochromic effect pigment of claim 1, comprising precipitating one or more inorganic metal oxides or metal oxide hydrates, or $BaSO_4$ in an aqueous medium onto the surface of an encapsulated thermochromic liquid crystal material suspended in said aqueous medium, and separating and drying the resulting pigment.

21. A process according to claim 20, wherein one or more metal oxides or metal oxide hydrates are precipitated together or one after another onto the surface of said liquid crystal material.

* * * * *